(12) United States Patent
Biggs et al.

(10) Patent No.: US 6,174,323 B1
(45) Date of Patent: *Jan. 16, 2001

(54) METHOD AND ASSEMBLY FOR LUNG VOLUME REDUCTION

(75) Inventors: Michael J. Biggs, San Francisco; Bryan Loomas, Saratoga; James M. Davenport, Fallbrook, all of CA (US)

(73) Assignee: Broncus Technologies, Inc., Mountain View, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/092,727

(22) Filed: Jun. 5, 1998

(51) Int. Cl.[7] .................................................... A61B 17/04
(52) U.S. Cl. ............................ 606/232; 606/233; 606/144
(58) Field of Search ........................... 606/167, 213–230, 606/232, 233, 144–150

(56) References Cited

U.S. PATENT DOCUMENTS

| | | |
|---|---|---|
| 5,507,754 * | 4/1996 | Green et al. ........................ 606/144 |
| 5,573,540 | 11/1996 | Yoon . |
| 5,573,543 | 11/1996 | Akopov et al. . |
| 5,749,899 * | 5/1998 | Bardin ................................. 606/232 |
| 5,810,848 | 9/1998 | Hayhurst . |
| 5,827,298 | 10/1998 | Hart et al. . |
| 5,865,791 | 9/1999 | Whayne et al. . |
| 5,868,762 | 2/1999 | Cragg et al. . |
| 5,908,429 | 6/1999 | Yoon . |
| 5,957,953 | 9/1999 | DiPoto et al. . |
| 5,972,022 | 10/1999 | Huxel . |
| 5,984,917 | 11/1999 | Fleischman et al. . |
| 6,003,517 | 12/1999 | Sheffield et al. . |
| 6,010,525 | 1/2000 | Bonutti et al. . |

* cited by examiner

Primary Examiner—Michael Buiz
Assistant Examiner—Lien Ngo
(74) Attorney, Agent, or Firm—Morrison & Foerster LLP

(57) ABSTRACT

A method and assembly for reducing the volume of a lung. A plurality of anchors are anchored at different positions in the lung. A cord is attached to each of the anchors. The anchors are drawn towards one another via the cords to cause the lung to collapse, thus compressing the tissue in the lung and establishing a reduction in lung volume.

47 Claims, 8 Drawing Sheets

METHOD AND ASSEMBLY FOR LUNG VOLUME REDUCTION

BACKGROUND OF THE INVENTION

1. Field of the Invention

The present invention relates to a method and assembly for reducing the volume of a lung and, more particularly, to a mechanical lung volume reduction assembly having cords and anchors that pull on portions of a lung to compress the volume of a portion of the lung.

2. Brief Description of the Related Art

The lungs deliver oxygen to the body and remove carbon dioxide. Healthy lung tissue includes a multitude of air passageways which lead to respiratory bronchiole within the lung. These airways eventually lead to small sacs called alveoli, where the oxygen and carbon dioxide are exchanged through the ultra-thin walls of the alveoli. This occurs deep within the lungs, in an area which is accessed by a network of airways, consisting of a series of branching tubes which become narrower, shorter, and more numerous as they penetrate deeper into the lungs. As shown in FIG. 1, tiny air sacs called alveoli 1 surround both alveolar ducts 2 and respiratory bronchiole 3 throughout the lung. The alveoli are small, polyhedral recesses composed of a fibrillated connective tissue and surrounded by a few involuntary muscular and elastic fibers. These alveoli 1 inflate and deflate with air when we breath. The alveoli are generally grouped together in a tightly packed configuration called an alveolar sac. The thin walls of the alveoli 1 perform gas exchange as we inhale and exhale.

During inhalation, as the diaphragm contracts and the ribs are raised, a vacuum is created in the chest, and air is drawn into the lungs. As the diaphragm relaxes, normal lungs act like a stretched balloon and rebound to the normal relaxed state, forcing air out of the lungs. The elasticity of the lungs is maintained by the supportive structure of the alveoli. This network of alveoli provides strength to the airway walls, as well as elasticity to the lungs, both of which contribute to the lung's ability to function effectively.

Patients with pulmonary disease have reduced lung capacity and efficiency due to the breakdown of lung tissue. This often is caused by smoking. In cases of severe chronic pulmonary disease, such as emphysema, lung tissue is destroyed, reducing the strength of the airways. This reduction and strength of the airway walls allows the walls to become "floppy" thereby losing their ability to remain open during exhalation. In the lungs of an emphysema patient, illustrated in FIG. 2, the walls between adjacent alveoli within the alveolar sac deteriorate. This wall deterioration is accelerated by the chemicals in smoke which affect the production of mucus in the lungs. Although the break down of the walls of the alveoli in the lungs occurs over time even in a healthy patient, this deterioration is greatly accelerated in a smoker causing the smoker's lungs to have multiple large spaces 4 with few connecting walls in the place of the much smaller and more dense alveoli spaces 1 in healthy lung tissue.

A cross section of a diseased emphysematous lung will look like Swiss cheese due to the deterioration of the alveoli walls which leaves large spaces in the tissue. In contrast, healthy lung tissue when seen in cross section has no noticeable holes because of the small size of the alveoli. When many of the walls of the alveoli 1 have deteriorated as shown in FIG. 2, the lung has larger open spaces 4 and a larger overall volume, but has less wall tissue to achieve gas exchange.

In this diseased state, the patient suffers from the inability to get the air out of their lungs due to the collapse of the airways during exhalation. Heavily diseased areas of the lung become overinflated. Within the confines of the chest cavity, this overinflation restricts the in-flow of fresh air and the proper function of healthier tissue, resulting in significant breathlessness. Thus, the emphysema patient must take in a greater volume of air to achieve the same amount of gas exchange. When severe emphysema patients take in as much air as their chest cavity can accommodate, they still have insufficient gas exchange because their chest is full of non-functional air filling large cavities in the lungs. Emphysema patients will often look barrel-chested and their shoulders will elevate as they strain to make room for their overinflated lungs to work.

In severe emphysema cases, lung volume reduction surgery (LVRS) is performed to improve lung efficiency of the patient and allow the patient to regain mobility. In lung volume reduction surgery, a more diseased portion of an emphysematous lung having a large amount of alveolar wall deterioration is surgically removed. LVRS is performed by opening the chest cavity, retracting the ribs, stapling off, and removing the more diseased portion of the lung. This allows the remaining healthier lung tissue to inflate more fully and take greater advantage of the body's ability to inhale and exhale. Since there is more air and more gas exchange in the healthier portion of the lung, lung efficiency is improved.

Lung volume reduction surgery is an extremely invasive procedure requiring the surgical opening of the chest cavity and removal of lung tissue. This surgery has substantial risks of serious post-operative complications, such as pneumothorax, and requires an extended convalescence.

Accordingly, it is desirable to achieve the benefits of improved air exchange for emphysema patients provided by LVRS without invasive open chest surgery and the associated complications.

SUMMARY OF THE INVENTION

The present invention relates to a minimally invasive system for reducing the volume of an emphysematous or otherwise unhealthy lung without the drawbacks of conventional LVRS.

In accordance with one aspect of the present invention, a method is described for reducing the volume of a lung. The method includes the steps of anchoring at a first position in the lung a first anchor, anchoring at a second position in the lung a second anchor, where the first position is distant from the second position, reducing the distance between the anchored first anchor and the anchored second anchor to decrease a volume of the lung, and preventing the reduced distance from substantially increasing.

In accordance with an additional aspect of the present invention, a method is described for reducing the volume of a lung. The method includes the steps of anchoring in a portion of a lung an anchor having a cord attached thereto, and pulling the cord to cause the anchor to pull on the portion of the lung to decrease the volume of the lung.

In accordance with a further aspect of the invention an assembly for reducing the volume of a lung is described. The assembly includes a first cord, and a first anchor for anchoring to a first portion of the lung. The first cord is attached to the first anchor. The assembly further includes a second cord, and a second anchor for anchoring to a second portion of the lung. The second cord is attached to the second anchor. The assembly also includes a delivery device for delivering the first anchor to the first portion of the lung and for delivering the second anchor to the second portion of the lung, and a connection device for connecting the first cord to the second cord within the lung.

In accordance with an additional aspect of the invention an assembly for reducing the volume of a lung is described. The assembly includes a first anchor for anchoring to a first portion of the bronchial passageways of the lung, and a second anchor for anchoring to a second portion of the bronchial passageways of the lung. The assembly also includes a connection device for positioning in the lung, a first cord connecting the first anchor to the connection device, and a second cord connecting the second anchor to the connection device, the connection device preventing the first cord and the second cord from moving relative to the connection device in a direction away from the connection device.

In accordance with another aspect of the invention an assembly for reducing the volume of a lung is described. The assembly includes a first anchor for anchoring to a first portion of the lung, a second anchor for anchoring to a second portion of the lung, and a connection device connected to the first anchor by a first cord and connected to the second anchor by a second cord. The first cord has a first cord length measured between the first anchor and the connection device. The second cord has a second cord length measured between the second anchor and the connection device. The connection device prevents the first cord length and the second cord length from increasing.

In accordance with a further aspect of the present invention, a method is described for reducing the volume of a lung with at least one of a first and second anchor, the method includes the steps of: connecting the first anchor to the second anchor with at least one cord; fixing the first anchor at a first portion of the lung; fixing the second anchor at a second portion of the lung; and tensioning the at least one cord to cause at least one of the first anchor and the second anchor to decrease the volume of the lung.

The present invention provides advantages of a minimally invasive procedure for surgically treating the effects of emphysema and other lung disease without the complications associated with conventional surgery.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

The present invention pertains to a method and assembly to relieve the effects of emphysema and other lung diseases by increasing the efficiency of gas exchange in the lung. This is achieved by compressing the volume of a portion of the lung, preferably at the diseased portion of the lung tissue. Compressing the volume of a portion of the lung redistributes the remaining healthier lung tissue to allow the remaining healthier lung tissue to inflate more fully. The reduction in volume of the portion of the lung also increases the range of motion of the diaphragm and chest wall thereby improving lung efficiency.

Figure 1:
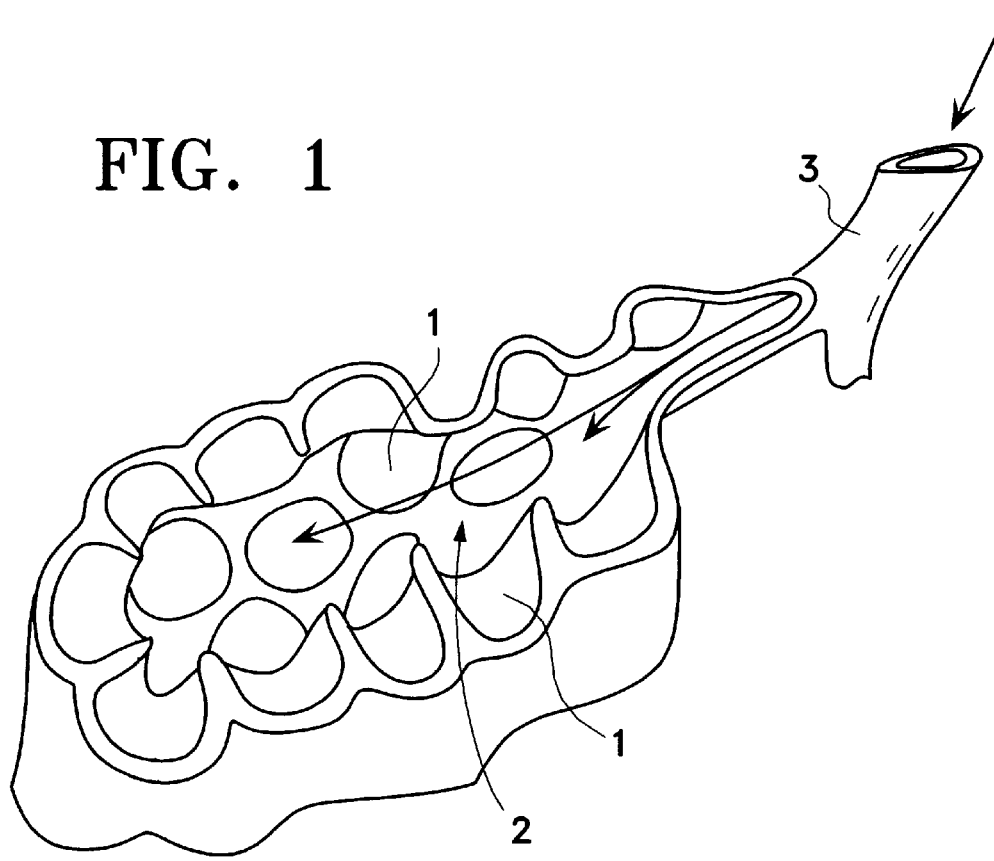
FIG. 1 is a cross sectional view of an alveolar sac of a healthy lung.
Figure 2:
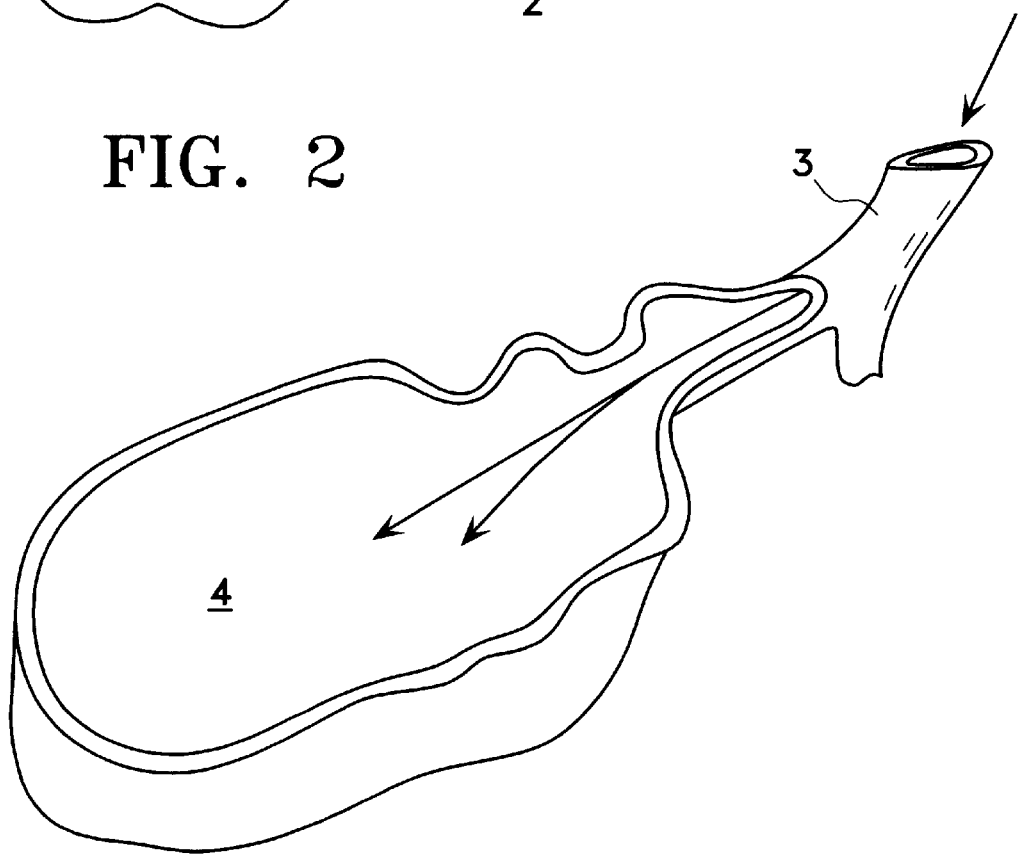
FIG. 2 is a cross sectional view of an alveolar sac of a diseased lung.
Figure 3:
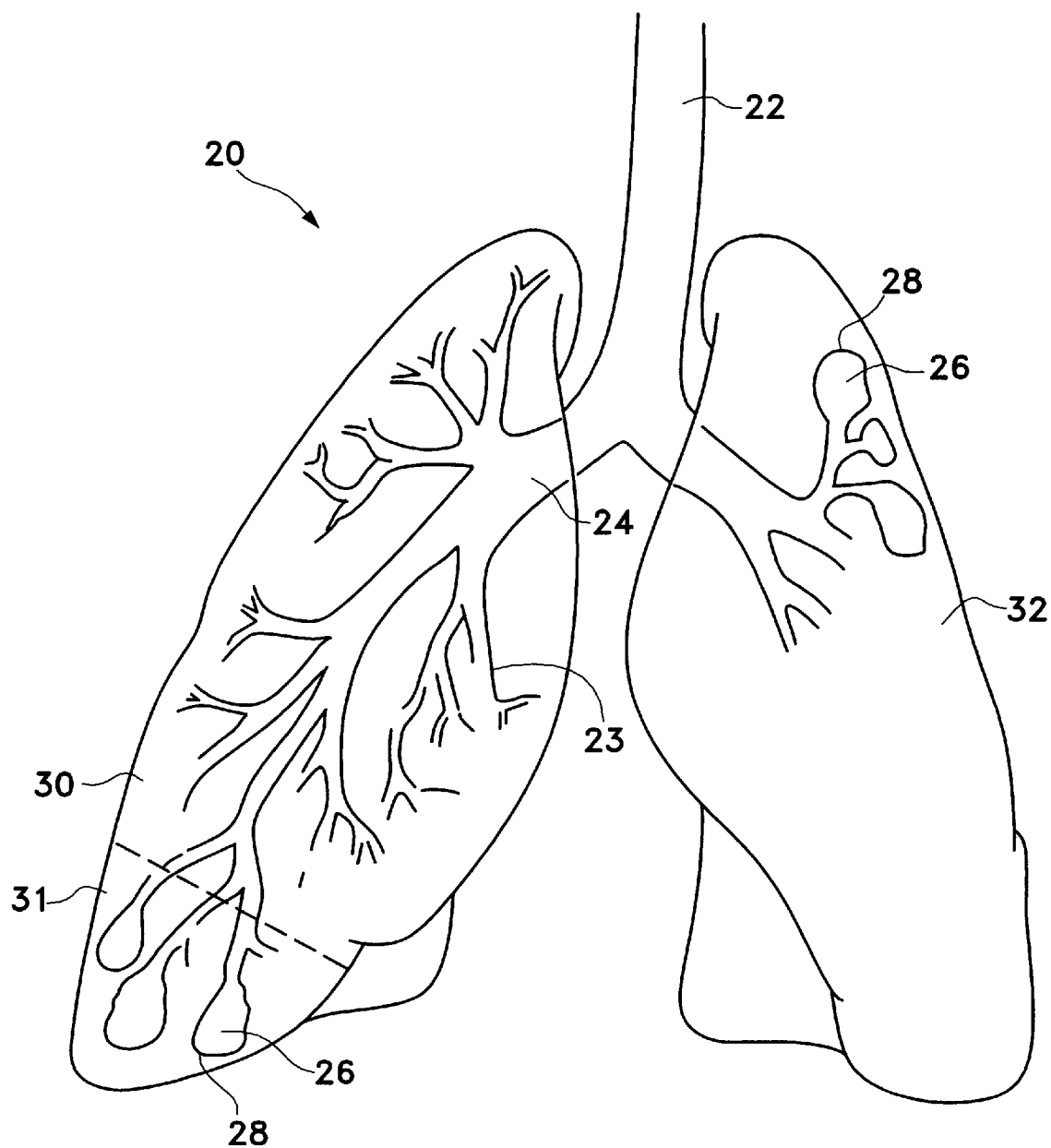
FIG. 3 is an illustration of a lung having a diseased lower portion prior to surgery.

FIG. 3 illustrates human lungs 20 having a left lung 30 and a right lung 32. A diseased portion 31 is located at the lower portion or base of the left lung 30 (indicated by the volume of the lung below the dashed line on the left lung). In actuality, the diseased portions of an unhealthy lung are not generally located in discrete areas. That is, the diseased portions are not distributed homogeneously, and are more heterogeneous.

As illustrated in FIG. 3, the trachea 22 extends down from the larynx and conveys air to and from the lungs. The trachea 22 divides into right and left main bronchi 24, which in turn form lobar, segmental, and sub-segmental bronchi or bronchial passageways. Eventually, the bronchial tree 23 extends to the terminal bronchiole. At the terminal bronchiole, alveolar sacs 26 containing alveoli 28 perform gas exchange as humans inhale and exhale.

As illustrated in FIG. 3, the diseased portion 31 of the lung 30 is located at the lower portion or base of the lung. By way of example, it can be considered that this diseased portion 31 has been stricken by emphysema. The emphysematous portion 31 of the lung 30 generally includes sections in which the walls between the adjacent alveoli 28 have deteriorated to a degree that the lung tissue looks like Swiss cheese in cross section. When this occurs, pulmonary function is impaired to a great degree by the lack of alveoli wall tissue which provides the gas exchange function of the lung. Because of the emphysema, the diseased portion of the lung loses its elastic recoil properties. Other sections of the emphysematous lung may include more healthy tissue and have less deterioration of alveoli walls. However, when the lungs inflate, air passes into both the healthy and unhealthy portions of the lungs. Because the walls of the alveoli in the emphysematous portion 31 of the lung 30 have deteriorated, there is less tissue through which to achieve gas exchange. Thus, the emphysema patient must take in a greater volume of air to achieve the same amount of gas exchange. The present invention strives to relieve the effects of emphysema by increasing the efficiency of gas exchange in the lung 30. As described below, the present invention increases the range of motion of the diaphragm and chest wall by compressing the volume of a portion of the lung occupied in the thoracic cavity to redistribute the remaining healthier lung tissue, thus improving the efficiency of gas exchange in the lung.

According to one embodiment of the present invention, the volume of a portion of a diseased lung is compressed or reduced by locating an anchor in a bronchial passageway of the lung, and then pulling on the anchor so as to collapse the lung tissue surrounding the anchor to compress the volume of a portion of the lung. Preferably, a plurality of anchors are used to assist in collapsing an area of the lung tissue.

Figure 4:
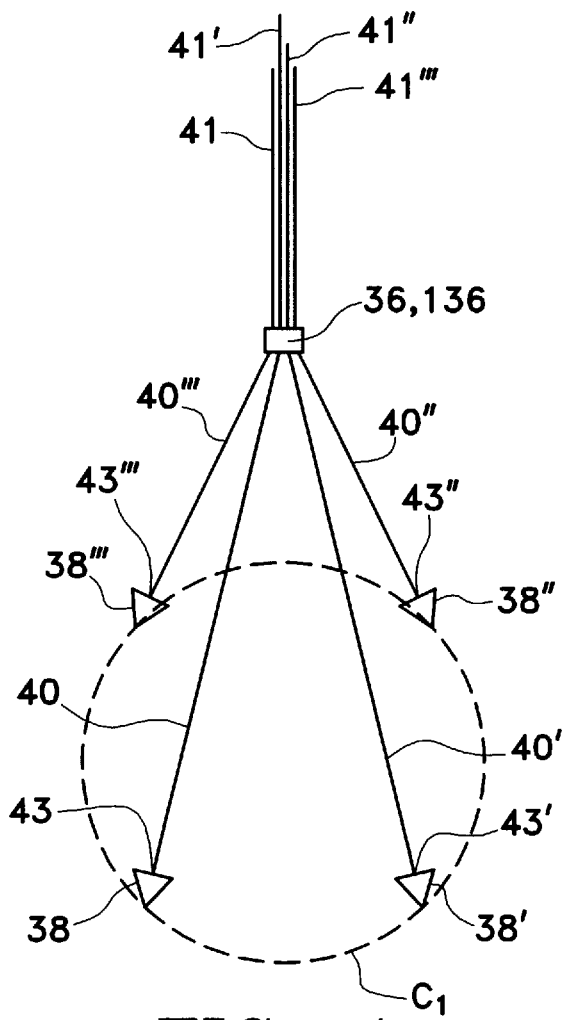
FIG. 4 is a perspective view of a plurality of anchored anchors before being pulled to compress the volume of a portion of a lung.
Figure 6:
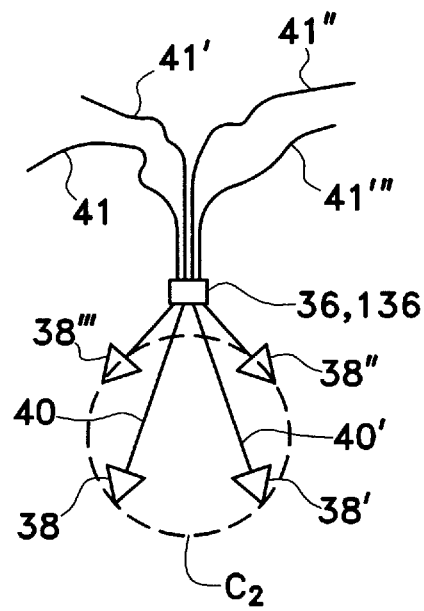
FIG. 6 is a perspective view of a plurality of anchored anchors after being pulled to decrease the compress the volume of a portion of a lung according to one embodiment of the present invention.
Figure 5:
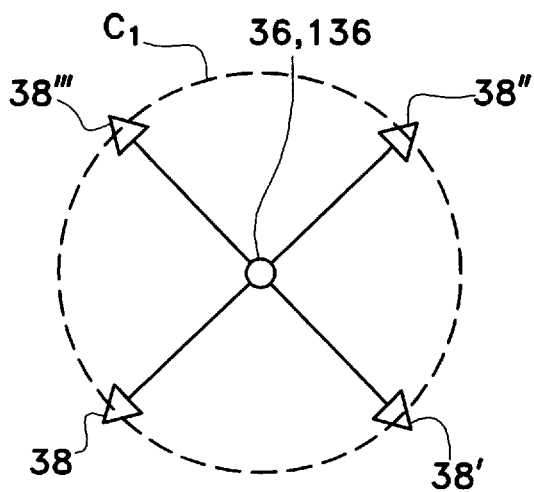
FIG. 5 is a top view of the plurality of anchored anchors shown in FIG. 4.
Figure 7:
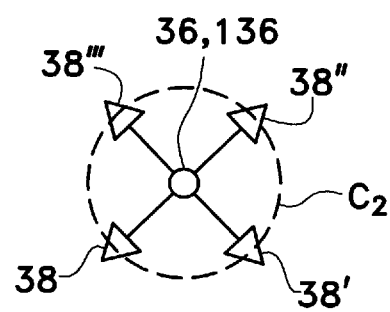
FIG. 7 is a top view of the plurality of anchored anchors shown in FIG. 6.

FIGS. 4–7 illustrate the general concept of the present invention. FIGS. 4 and 5 represent a time $t_1$, and FIGS. 6 and 7 represent a later point in time $t_2$. At time $t_1$, a plurality of anchors 38, 38', 38", 38'" are located at different positions in the lung. The anchors 38, 38', 38", 38'" are anchored, fixed, or firmly attached to the lung (not illustrated) at their respective different positions. Thus, the area of the lung that is immediately surrounding each anchor will move when the respective anchor is moved.

The anchors 38, 38', 38", 38'" are equally spaced as shown in FIGS. 4 and 5. However, the anchors may be located at various positions in the lung so as to not be evenly or equally spaced and still function to compress the volume of a portion of the lung as described herein. Attached to each of the anchors 38, 38', 38", 38'" is a cord 40, 40', 40", 40'" which can be in the form of a string, fiber, filament, rubber band, coil spring, or the like. Each of the cords 40, 40', 40", 40'" has a free end 41, 41', 41", 41'" and an attached end 43, 43', 43", 43'". The attached end 43, 43', 43", 43'" of the cords is that end of each respective cord 40, 40', 40", 40'" that is attached or tethered to the respective anchors 38, 38', 38", 38'". The free ends 41, 41', 41", 41'" of each cord 40, 40', 40", 40'" is the most distal end of the cords that is not attached to the respective anchors 38, 38', 38", 38'".

As shown in FIGS. 4–7, the anchors 38, 38', 38", 38'" generally lie along the circumference of a circle $C_1$. Although the anchors 38, 38', 38", 38'" are illustrated as lying along the circumference of a circle, the anchors can be located in other configurations, so long as the anchors are separated from each other. Thus, the anchors can be anchored in different planes and spaced apart from each other in a variety of different configurations.

The circle $C_1$ has an area $A_1$. Each of the cords 40, 40', 40", 40'" is attached to a respective anchor 38, 38', 38", 38'". For example, the cord 40' is attached to the anchor 38'. Each of the cords 40, 40', 40", 40'" is connected to a connection device 36. The connection device 36 connects, knots, unites, bonds, fastens, glues, wedges, attaches, or fixes together the cords 40, 40', 40", 40'" such that when one of the cords 40 attached to an anchored anchor 38 is pulled in tension, the other cords 40', 40", 40'" are also placed in tension. The connection device 36 is thus connected to the first anchor 38 by the first cord 40 and is connected to the second anchor 38' by the second cord 40'. In essence, when two cords 40, 40' are connected by the connection device 36, the two cords 40, 40' between the two anchors 38, 38' and the connection device 36 together function as or define one cord connecting to the two anchors 38, 38'. Thus, the connecting device 36 may can be a clasp, clamp, cinch, snap, knot, clip, chock, self-locking device, or the like.

The first cord 40 has a first cord length measured between the first anchor 38 and the connection device 36. The second cord 40' has a second cord length measured between the second anchor 38' and the connection device 36. The other cords 40", 40'" passes cord lengths measured between the respective anchor and the connection device 36. The connection device 36 prevents each of the cord lengths from increasing, i.e., prevents the anchors from returning to their original anchored positions. The embodiment of the connection device 36 illustrated in FIGS. 4–7 is a self-locking device, described further below, that permits each of the cords 40, 40', 40", 40'" to traverse away from the self-locking device in a direction toward the free ends 41, 41', 41", 41'", but prevents each of the cords from traversing away from the self-locking device in a direction toward the attached ends 43, 43', 43", 43'". The cords 40, 40', 40", 40'" pass through an opening in the self locking device.

The cords 40, 40', 40", 40'" illustrated in FIGS. 4 and 5 have just been pulled taut. That is, the cords 40, 40', 40", 40'" have been pulled or drawn tight and are not slack. However, at the time $t_1$ illustrated in FIG. 4., the anchors, and surrounding lung tissue, have not been moved. Thus, the lung has not been compressed and the volume has not been changed. However, after the cords 40, 40', 40", 40'" are taut and the cords are pulled or further tensioned, the distance between the anchors 38, 38', 38", 38'" will decrease. The lung tissue surrounding each anchor 38, 38', 38", 38'" moves with the respective anchor such that the lung tissue will physically collapse or compress. The connection performed by the connection device 36 may occur while the distance between the anchors 38, 38', 38", 38'" is decreased, or after the distance between the anchors has been decreased to a desired distance. According to one embodiment of the present invention, a self-locking device is moved toward the anchors 38, 38', 38", 38'" to cause the distance between the anchors to decrease, and at each point along the path of movement of the connection device a connection between the cords 40, 40', 40", 40'" is defined.

Thus, as illustrated by FIGS. 6 and 7, at time $t_2$, the anchors 38, 38', 38", 38'" and surrounding lung tissue have been moved toward each other (toward the center of the original circle $C_1$) to define a second circle $C_2$ having a smaller diameter than the circle $C_1$. At time $t_2$ the anchors 38, 38', 38", 38'" generally lie along the circumference of the circle $C_2$. As described above, this may be achieved by pulling the anchors 38, 38', 38", 38'" toward each other via the cords 40, 40', 40", 40'". As described farther below, the anchors can be pulled or moved toward each other by: (1) pulling the free ends 41, 41', 41", 41'" of the cords away from a self-locking device; (2) moving the self-locking device 136 toward the anchors 38, 38', 38", 38'" to pull the anchors; or (3) simultaneously moving the self-locking device toward the anchors and pulling the free ends of the cords away from the self locking device.

Because the diameter of the second circle $C_2$ is smaller than the diameter of the circle $C_1$, the area of the second circle is smaller than the area of the first circle. Because the area of the second circle $C_2$ is smaller than that of the first circle $C_1$ (and the distance between the anchors 38, 38', 38", 38'" has decreased), the lung tissue near the anchors will collapse or compress inwardly toward the center of the circles $C_1$, $C_2$. Depending upon the location of the anchors 38, 38', 38", 38'", the anchors can move inwardly toward the center of the circles and slightly toward the center or interior of the lung. Because he distance between the anchors 38, 38', 38", 38'" has been decreased, the net surface area or peripheral surface of the portion of the lung is less, and the volume of the lung is less due to the collapsing or compressing of the lung tissue.

Figure 11:
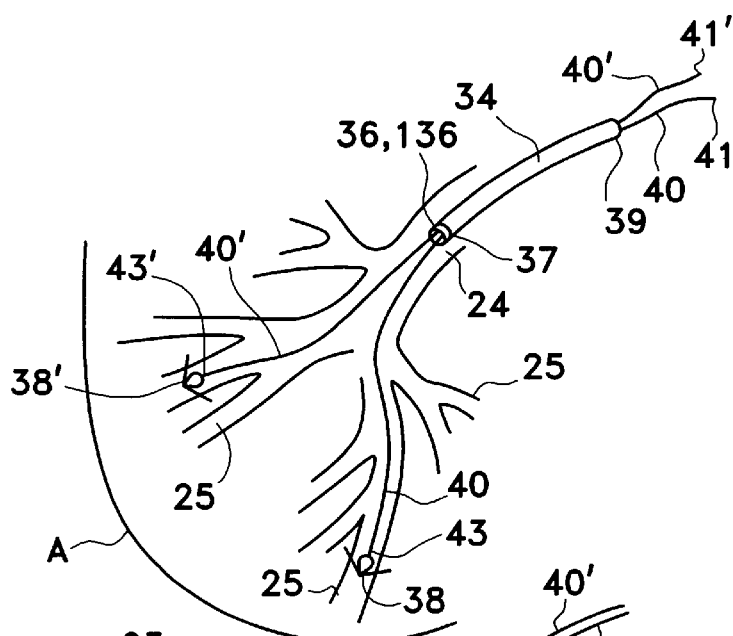
FIG. 11 is an illustration of a portion of a lung before its volume has been reduced or compressed.
Figure 12:
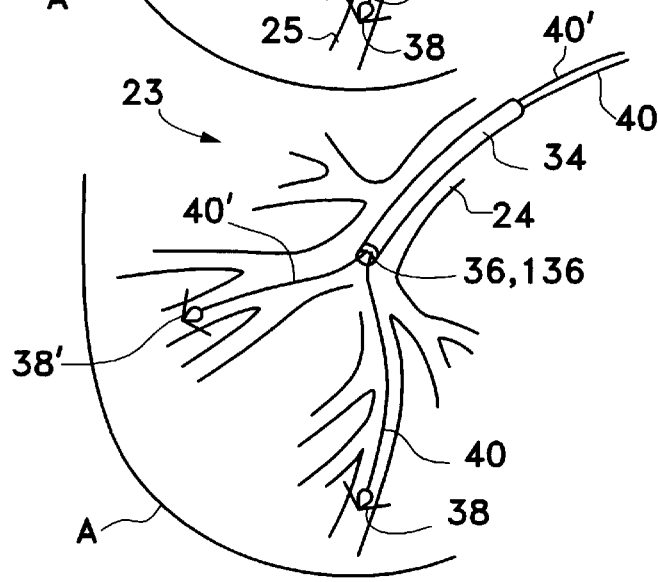
FIG. 12 is an illustration of a portion of a lung before its volume has been reduced.
Figure 13:
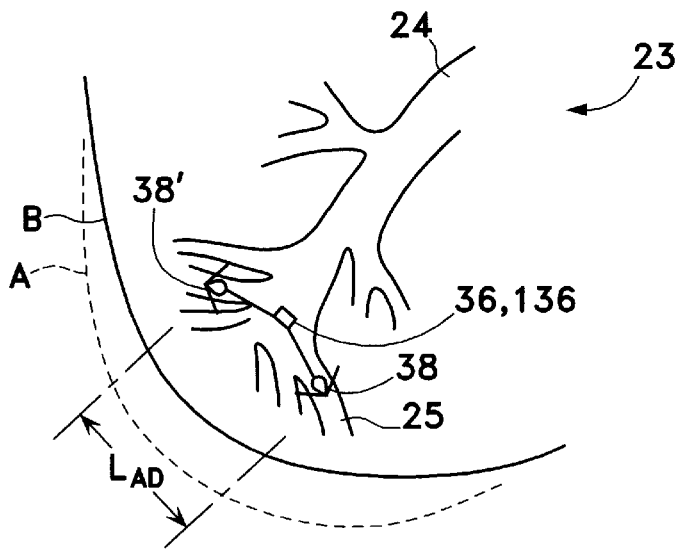
FIG. 13 is an illustration of a portion of a lung after its the volume has been reduced according to one embodiment of the present invention.

After the portion of the cords 40, 40', 40", 40'" between the connection device 36 and the anchors 38, 38', 38", 38'" is tensioned and the connection device 36 has connected the cords so as to keep the lung tissue in its collapsed condition, the remaining portion of the cords having the free ends 41, 41', 41", 41'" (the limp portions illustrated in FIG. 6) are cut such that non-functional portions of the cords may be removed from the lungs by pulling the cords out of the mouth or nasal cavity. FIGS. 11–13 illustrate in further detail how the diseased portion of a lung 31 may be collapsed to reduce the volume of the lung 30.

Figure 8:
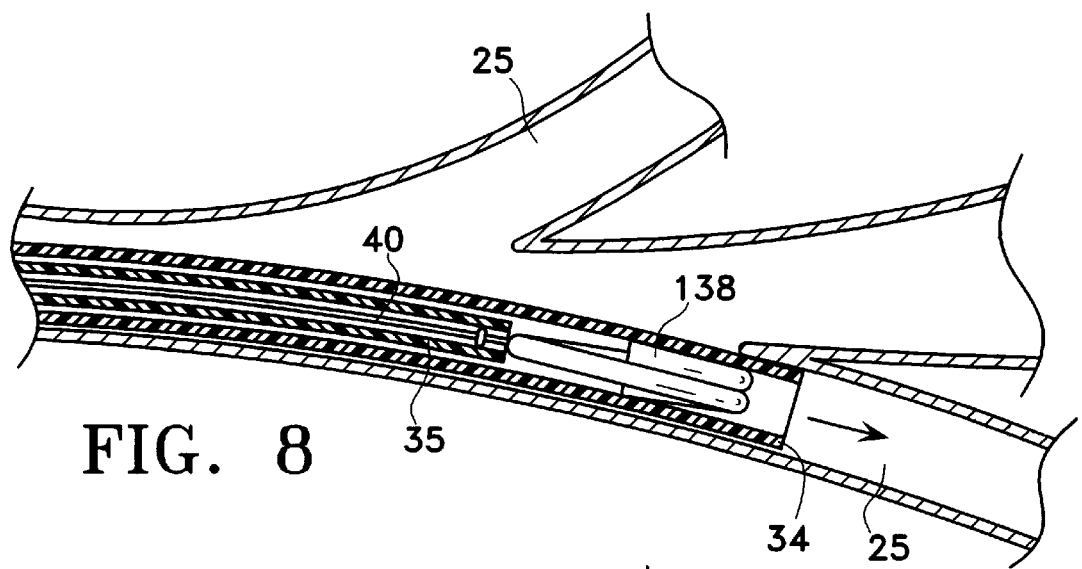
FIG. 8 is a side cross sectional view of an anchor being inserted into a bronchial passageway according to one embodiment of the present invention.
Figure 9:
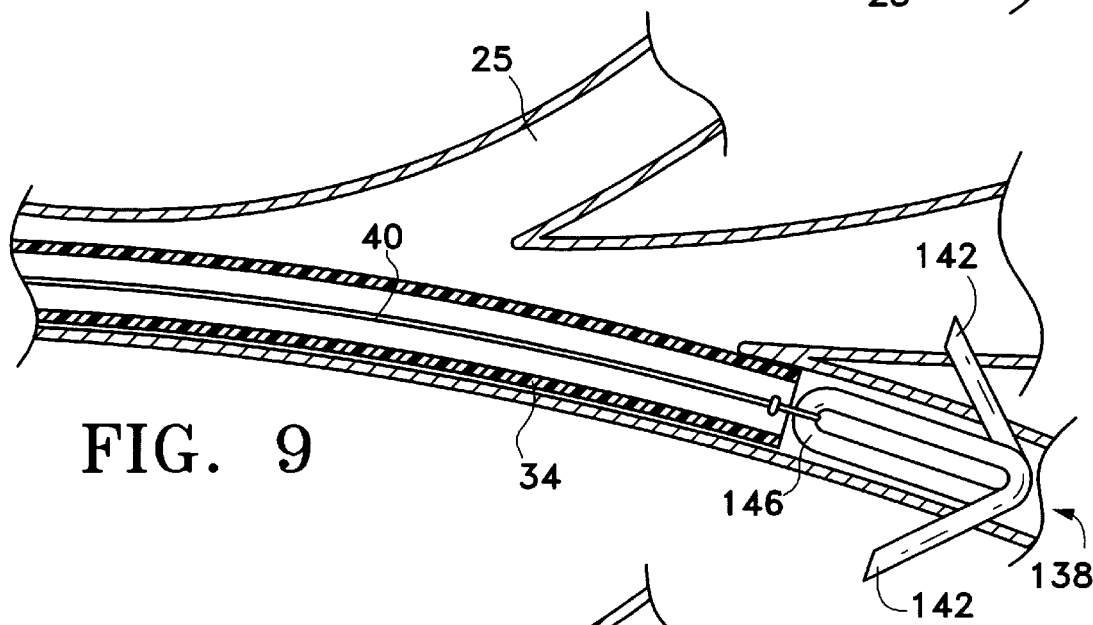
FIG. 9 is a side cross sectional view of an anchor anchored to a bronchial passageway according to one embodiment of the present invention.
Figure 10:
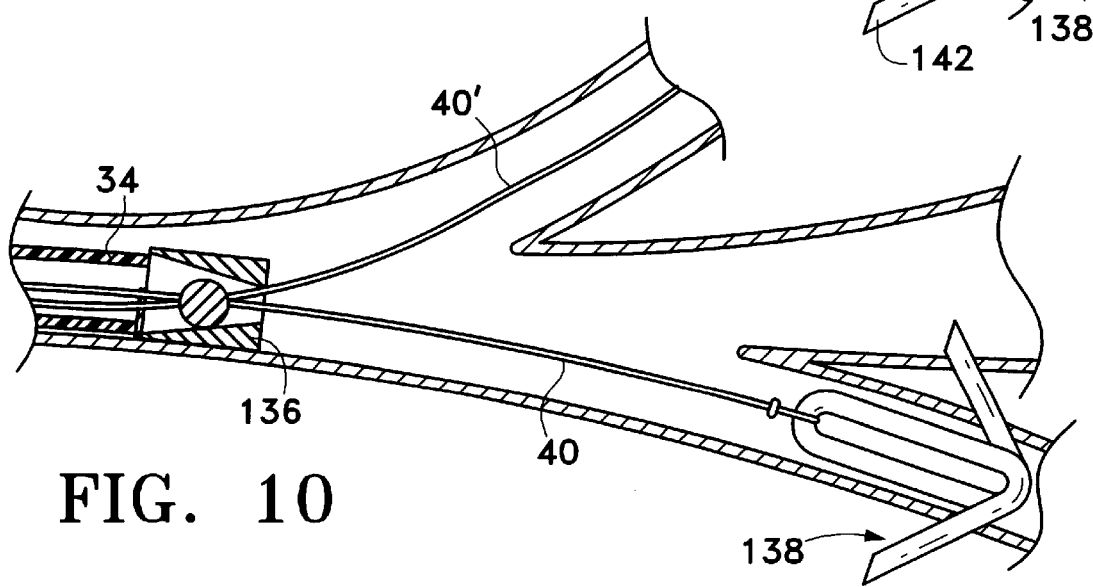
FIG. 10 is a side cross sectional view of an anchor fixed to a bronchial passageway and tethered to a self-locking device according to one embodiment of the present invention.

As illustrated by FIG. 11, the bronchial tree-like pattern 23 in the lung 30 includes a multitude of bronchial passageways 25. Any of these bronchial passageways 25 may be used to insert an anchor 38 into the lung. Because the bronchial passageways 25 are hollow, it is possible to insert a delivery device such as the tube 34, a bronchoscope, or a cannula into one bronchial passageway. As shown in FIG. 11, the lung 31 includes therein a pair of anchors 38, 38' which have been anchored or attached to two separate bronchial passageways 25 in the outer periphery of the bronchial tree 23. Attached to each of the anchors 38, 38' is a cord 40, 40' that extends from each of the anchors 38, 38' through the bronchial tree 23 and into the tube 34. One cord 40, 40' is tethered to each of the anchors 38. The line or cord 40, like the cannula 34, extends through the bronchus 24 up the trachea 22 and out the mouth or nasal cavity of the patient. FIGS. 8–10 illustrate in greater detail how the anchors 38, 38', are located in and fixed to the outer periphery of the bronchial tree.

As shown in FIG. 8, the bronchial passageway 25 is large enough to receive the tube 34. The delivery device or tube 34 is used to deliver the anchor 38 to the outer periphery of the bronchial tree. Specifically, the anchor 38 to be delivered to the outer periphery of the bronchial tree is located inside the cannula 34. A bronchoscope is the preferred delivery device. Bronchoscopes have visualization optics which permit an operator to determine where the anchor should be placed. After the proper location has been determined with the bronchoscope, the anchor 38 is delivered through the airway of the bronchoscope.

According to the embodiment shown in FIG. 8, the anchor is a V-shaped spring 138. The V-shaped spring 138 is in a collapsed state while inside the tubular channel of the tube 34. When the V-shaped spring 138 is located within the tube 34, the V-shaped spring will remain in its collapsed state. When the V-shaped spring 138 is pushed outside of the tube 34, the V-shaped spring will expand to its expanded position, as shown in FIG. 9. Once the V-shaped spring 138 expands, it is fixed or fastened to the walls of the bronchial passageway 25 such that the lung tissue in the vicinity of the V-shaped spring moves with the V-shaped spring. A hollow second tube or a push-device 35 having a size or diameter smaller than that of the internal diameter of the tube 34 is inserted into the tube 34 to force the V-shaped spring 138 through the length of the tube 34 and out of the tube 34 into the bronchial passageway 25.

Figures 14, 15:
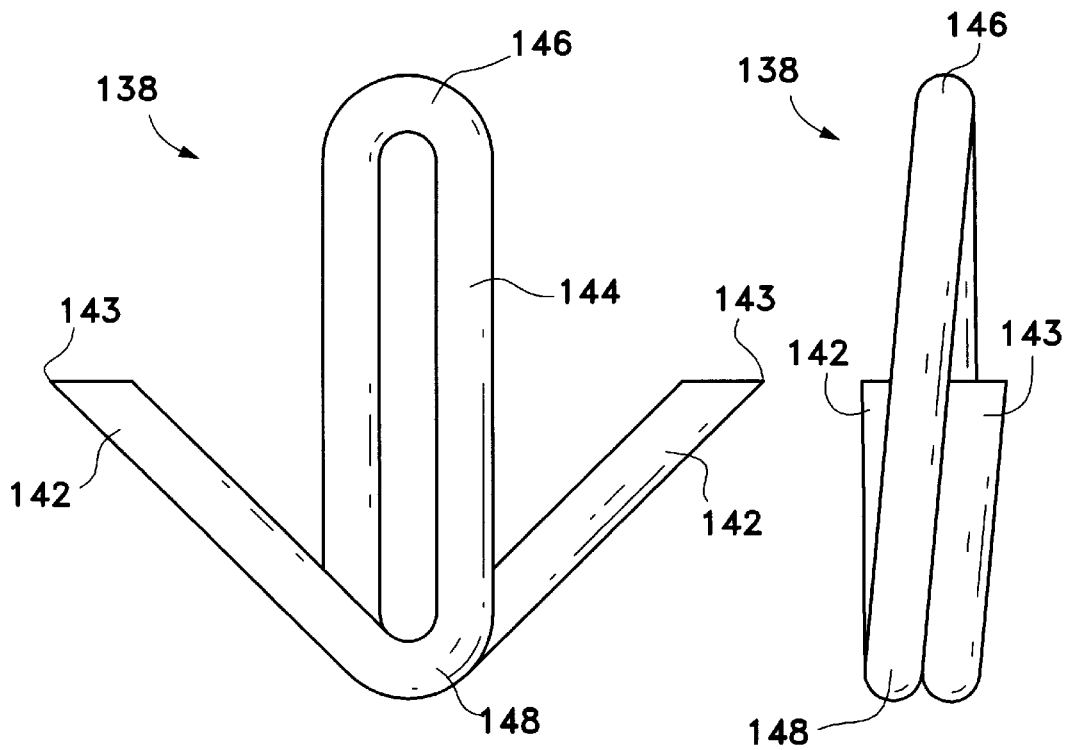
FIG. 14 is a side view of an anchor for use with the present invention.
FIG. 15 is an end view of the anchor of FIG. 14.
Figure 16:
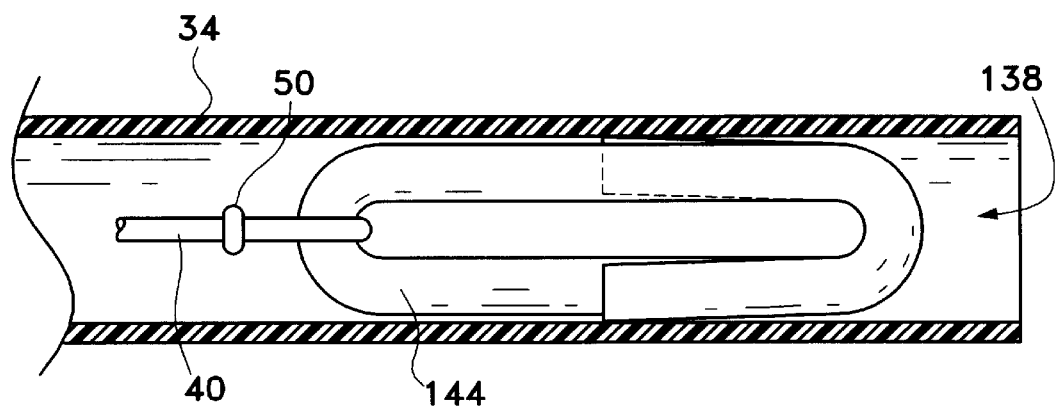
FIG. 16 is a side cross sectional view of an anchor according to one embodiment of the present invention, where the anchor is in a collapsed state and is located within a tube.

FIGS. 14–16 illustrate further details of the V-shaped spring 138. As shown in FIG. 14, the V-shaped spring 138 is a rod shaped piece that has been bent such that it has spring-like characteristics. The V-shaped spring 138 includes two end portions or barbs 142 that form an angle relative to a lateral portion 144 of the V-shaped spring when the barbs are in the extended position. The barbs 142 together define the V-shape of the V-shaped spring when the barbs are in an expanded position. Hence, the barbs 142 together define the point or vertex of the "V" at an insertion end 148 of the V-shaped spring.

The barbs 142 perform the anchoring function of the V-shaped spring 138 by wedging against the bronchial passageway to create friction or by penetrating into the walls of the bronchial passageway. Because of the spring-like characteristics of the V-shaped spring, the barbs 142 strive to angle outwardly from the lateral portion 144. The barbs 142 extend outwardly away from the insertion end 148 of the V-shaped spring. The V-shaped spring 138 also includes an attachment end 146 located opposite from the insertion end 148. The attachment end 146 is the location where one of the cords 40 is tethered. Because the barbs 142 strive to extend angularly outward from the lateral portion 144, and form an angle with respect to the lateral portion, the V-shaped spring 138 is preferably inserted into the tube 34 insertion end 148 first such that the attachment end 46 follows (see FIGS. 8 and 9). Thus, the insertion end 148 of the V-shaped spring 138 will be the first portion of the V-shaped spring that exits the tube 34 as the push device 35 forces the V-shaped spring from the tube. The attachment end 146 of the V-shaped spring 138 is the last portion of the V-shaped spring to exit from the tube 34.

As soon as the barbs 142 extend from the tube 34, they will spring outwardly toward the walls of the bronchial passageway. The barbs 142 of the V-shaped spring 138 prevent the expanded V-shaped spring from moving in a direction opposite to the direction in which the "V" or vertex points. That is, the barbs 142 function similar to barbs on a fish hook, harpoon, or arrow. The barbs 142 each include a sharp point 143 that curves or projects in a direction opposite from the direction the vertex at the insertion end 148 points.

Although the V-shaped spring 138 illustrated in FIGS. 14 and 15 is the preferred embodiment of the anchor 38, other similar anchoring devices can be used to perform the same function. For example, a J-hook, a mooring device, a ballooning device, and expanding polymeric plug, a stent-like device, and other various devices can be satisfactorily fastened, fixed or anchored to the bronchial passageway of a lung. Furthermore, although the V-shaped springs include two barbs 142, the V-shaped spring can have more than two barbs or only one barb. In addition, the connection device 36 can also anchor to the lung. For example, two cords 40, 40' having anchors 38, 38' attached thereto can be tied to a third anchor such that the third anchor is a connection device, As shown in the end view of the V-shaped spring 138 in FIG. 15, the end profile of the V-shaped spring 138 is thin as compared to the side profile illustrated in FIG. 14. Although not necessary, the profile of the V- shaped spring 138 permits air and gases to pass through the bronchial passage in which the V-shaped spring is positioned.

FIG. 16 illustrates a side view of the V-shaped spring 138 in its collapsed position when the V-shaped spring is located within the tube 34. As shown in FIG. 16, the barbs 142 collapse toward the lateral portion 144 when the V-shaped spring 138 is positioned within the tube 34. Prior to inserting the V-shaped spring 138 into the tube 34, the cord 40 is secured to the attachment end 146 of the V-shaped spring. The cord 40 can be tethered, braided, buttoned, interlocked, wired, pinned, clasped, or joined to the attachment end 146 by any suitable means. The cord 40 may be wrapped around the attachment end 146 and secured to itself to define a loop around the attachment end 146. A clasp 50 or other similar device may be used to secure the loop around the attachment end 146.

Referring back to FIG. 8, the cord 40 has already been attached to the V-shaped spring 138 before the V-shaped spring has been located in the channel of the tube 34. Once the push device 35 pushes the V-shaped spring 138 out of the tube 34, the push device 35 is withdrawn, leaving the V-shaped spring 138 anchored or secured to the bronchial passageway 25. FIG. 9 illustrates that the cord 40 remains attached to the V-shaped spring 138 after the push device 35 has been withdrawn from the tube 34 and after the V-shaped spring has expanded. The protruding ends 42 of the V-shaped spring 138 extend into the walls of the bronchial passageway 25 such that the V-shaped spring 138 is fixedly secured to the bronchial passageway. Thus, substantial relative movement between the anchored V-shaped spring 138 and the portion of the bronchial passageway immediately adjacent the V-shaped spring does not occur; when the anchored V-shaped spring 138 moves, the surrounding tissue immediately adjacent to the V-shaped spring will move.

Once the V-shaped spring 138 is anchored in place, the tube 34 can be withdrawn from the bronchial passageway 25. Thereafter, the same procedure can be followed to deposit more V-shaped springs 138 (each having a cord 40 attached thereto) in other bronchial passageways at locations distant from the area where the first V-shaped spring was positioned. In reference to FIG. 10–13, after the anchors 38, 38', such as V-shaped springs, have been fixed to different positions in the bronchial tree, the cords 40, 40' can be tensioned.

Figure 17:
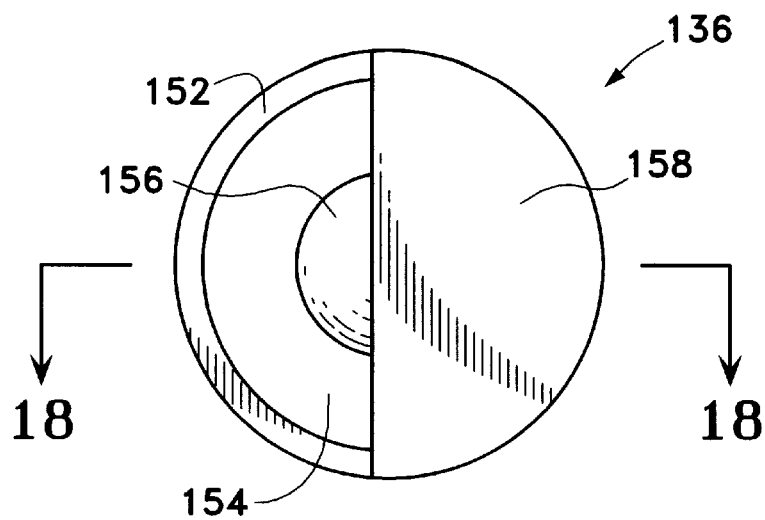
FIG. 17 is a top view of a self-locking device according to one embodiment of the present invention.
Figure 18:
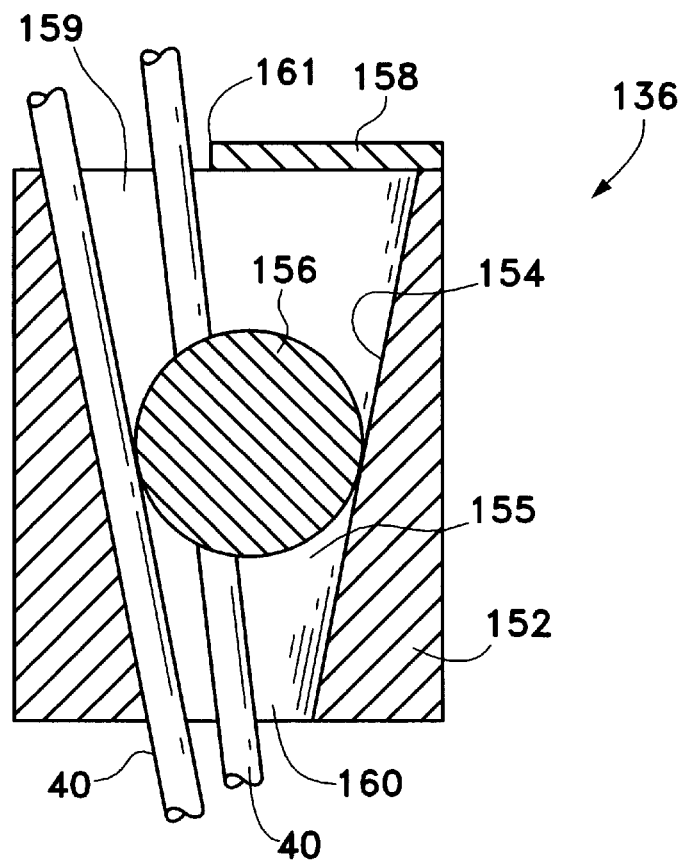
FIG. 18 is a side cross sectional view of the self-locking device of FIG. 17 taken along the line 18—18 of FIG. 17.

Once the anchors 38, 38' have been positioned in the lung, the connection device 36 is positioned to cause the cords 40, 40' to be tensioned and to move the anchors 38, 38'. The connection device 36 can be used to connect the cords 40, 40' and to cause the anchor 38 to move toward the anchor 38', thereby causing the tissue adjacent the anchor 38 to move towards the lung tissue adjacent the anchor 38'. FIGS. 17 and 18 illustrate one embodiment of the connection device 36.

FIGS. 17 and 18 illustrate a chock or self-locking device 136. The self-locking device 136 is configured to permit each of the cords 40, 40' to traverse away from the self-locking device in a direction toward the free ends 41, 41', and is also configure to prevent each of the cords 40, 40' from traversing away from the self-locking device in a direction toward the attached ends 43, 43' of the cords 40, 40'. The self-locking device 136 includes a passageway or channel 155 extending completely through the self-locking device, from a first opening 159 to a second opening 160. The cords 40, 40' pass through the openings 159, 160 and hence through the channel 155 in the self-locking device 136. The self-locking device 136 prevents the cords 40, 40' from being pulled back toward the anchors 38, 38'. When the self-locking device is located in the lung, it only permits the portion of the cords 40, 40' in the channel 155 to travel or be displaced relative to the self-locking device in a direction toward the trachea, not toward the outer periphery of the bronchial tree where the anchors 38, 38' are located.

In general, the self-locking device 136 allows the cords 40, 40' to pass in one direction, but locks the cords in place when they are forced to move the in the other direction. The self-locking device 136 includes a cylindrical body 152 having a tapered inner wall 154 that extends through the body 152 to define the conical channel 155. Thus, as shown in FIG. 18, the tapered inner bore 154 defines a conical interior. A ball 156 rests in the channel 155 and is retained therein by a cap or cover 158 located over the larger end of the taper. The cover 158 preferably covers the larger end of the bore to such an extent that the area of the first opening 159 is smaller that the cross-sectional area of the ball 156. However, the opening 159 should be large enough to permit at least one line 40 to pass through the first opening. In the embodiment illustrated in FIG. 18, the first opening 159 is large enough to permit two cords 40, 40' to pass therethrough. Because the cover 158 does not completely cover the larger bore diameter of the conical channel 155, the cords 40, 40' will fit through the gap or first opening 159 between the wall 154 and the edge 161 of the cover 158. Thus, the cords 40, 40' fit through the gap 159. Other embodiments of the self-locking device 136 may be configured to receive more than two cords.

The self-locking device 136 is dimensioned and configured such that when a cord 40 is pushed or pulled through the smaller second opening 160 (or smaller bore), the cord 40 will displace the ball 156 toward the cap 158 just enough for the line to continuously pass through the self locking device. When the line 40 is pushed or pulled in the opposite direction, the ball 156 will displace towards the smaller second opening 160, i.e., away from the cap 158. Because the ball 156 has a larger cross-sectional area than that of the smaller second opening 160, the ball will wedge against the conical inner wall 155 and the cord 40, locking, wedging, or chocking the cord in place. For example, if the cord 40 is pulled toward the cover 158, the self-locking device 136 will permit the line to be pulled in this direction. However, if the line 40 is pulled in the opposite direction away from the cover 158, the ball 156 will wedge against the line 40 and the inner wall 154 such that the line 40 cannot travel relative to the self-locking device 136. This wedging effect occurs because of the friction between the ball 156, the line 40, and the wall 154.

As described above, and as shown in FIG. 18, the self-locking device 136 is configured for two cords 40, 40'. The self-locking device 136 will self-lock two cords 40, 40' and only permit the lines 40, 40' to be moved in the direction toward the cover 158. When the self-locking device 136 is used in the present invention, the direction toward the cover 158 is also the direction towards the trachea, away from the position where the self-locking device is located. Although the function of the self locking device 136 has been described in reference to the cords 40, 40' being pushed or pulled, it should be recognized that the self-locking device prevents relative movement between the cords 40, 40' and the self-locking device in one direction and permits relative movement in the opposite direction, regardless if the cords alone, the device alone, or the cords and the device are pushed or pulled.

Although the self-locking device 136 illustrated in FIGS. 17 and 18 is the preferred embodiment of the connection device 36, other connection devices that have a locking, chocking, or wedging function are contemplated. For example, a connection device may include a plurality of tapered inner bores 154 and balls 156 each configured to receive and lock one line 40, rather than two lines 40, 40'. Additionally, other self-locking, chocking, or wedging devices such as devices similar to those used on sailing and marine vessels would also perform adequately.

Furthermore, as described earlier, the connection device 36 need not have a self-locking function. The connection device 36 need only substantially prevent the first cord length (measured between the first anchor 38 and the connection device 36) and the second cord length (measured between the second anchor 38' and the connection device 36) from increasing. This result occurs because the connection device 36 does not allow relative movement between connected cords 40, 40' with respect to the connection device when the connection device connects or fixes together the cords 40, 40'. Hence, after the cords 40, 40' have been connected and when the first cord 40 is forced in a state of tension or is pulled, the second cord 40' will also be forced in a state of tension or will be pulled. As described earlier, the connection device 36 can also function as an anchor, or the anchor 38 can function as a connection device. For example, the self-locking device 136 can include a plurality of barbs or a hook such that it can be anchored to a bronchial passageway or a bifurcation between two airways.

Referring again to FIGS. 10–13, after the anchors 38, 38' have been fixed or lodged in different positions in the bronchial tree, the cords 40, 40' can be tensioned. FIGS. 10–13 illustrate how the anchors 38, 38' may be used to collapse the tissue of the lung to decrease the volume of the lung. As described earlier, the anchors 38, 38' may be lodged in the outer periphery or most distal part of the bronchial tree through a tube 34 or a standard bronchoscope inserted through the mouth or nose of the patient. After the anchors 38, 38' are in place, the cords 40, 40' are gathered together and the free ends 41, 41' are inserted into the first end 37 of the tube 34, which may be the same tube that was used to deliver the anchors 38, 38', or a different tube. The gathered cords 40, 40' are received by the tube 34 until the free ends 41, 41' protrude from the second end 39 of the tube 34. The first end 37 of the tube 34 is then inserted into the trachea and into the bronchial tree towards the lodged anchors 38, 38'. FIG. 11 illustrates the tube 34 first entering the bronchial tree. FIG. 12 illustrates the tube 34 positioned farther into the bronchial tree towards the anchors 38, 38'. The free ends 41, 41' are preferably prevented from entering the lung while the tube 34 is being inserted into the lung with the cords 40, 40' therein. At this point in time, as illustrated by FIGS. 11 and 12, the lung has not been collapsed and is in its original position A.

Then, as illustrated in FIG. 13, at least one of the cords 40, 40' is pulled in tension such that the distance between the first anchor 38 and the second anchor 38' ("the anchor distance $L_{AD}$") decreases; this decrease in distance between the lodged anchors is what causes the volume of the lung to decrease. The more the anchors 38, 38' are drawn toward each other, the more the volume of the lung will decrease. By tensioning the lines 40, 40' the anchors 38, 38' will pull on the lung tissue in the direction toward the median between the anchors. The more the anchor distance $L_{AD}$ decreases, the more the lung tissue will collapse to decrease the volume of the lung. However, because the lung is generally elastic and will strive to return to its original position, it is necessary to maintain the decreased anchor distance $L_{AD}$ with the connection device 36 by connecting the cords 40, 40' to each other before the anchors have the opportunity to return to their original position. The connection device 36 connects the cords 40, 40' such that the reduced anchor distance $L_{AD}$ is maintained. For example, a small clasp or clamp will suffice to connect the cords 40, 40' together. Once the cords 40, 40' are connected by the connection device 36 and the reduced anchor distance is maintained, the cords 40, 40' will remain in tension due to the elastic properties of the lung. As shown in FIG. 13, the lung tissue has been partially collapsed or compressed to the new position B from the original position A. Thus, the volume of a portion of the lung has been compressed or decreased in accordance with one embodiment of the present invention.

The tube 34, or another similar device, can be used to locate or position the connection device 36 into the interior of the lung along the bronchial tree toward the anchors 38, 38'; this can occur before, during, or after the anchor distance $L_{AD}$ has been decreased. After the anchor distance $L_{AD}$ has been decreased by pulling the anchors 38, 38' towards one another via at least one of the cords 40, 40', the connection device 36 connects the cords such that the anchor distance $L_{AD}$ is maintained and the lung volume remains reduced. Thereafter, the portions of the cords 40, 40' between the connection device 36 and the free ends 41, 41' are cut or broken from the tensioned portions of the cords 40, 40' that maintain the reduced anchor distance $L_{AD}$. The cut portion of the cords 40, 40' having the free ends 41, 41' is removed from the reduced volume lung. The tube 34 is also removed from the reduced volume lung. The cords 40, 40' can be cut by a variety of techniques well known in the art. The anchors 38, 38', spaced from each other by the reduced anchor distance $L_{AD}$, and the tensioned cords 40, 40' remain in the reduced volume lung, preferably for the life of the patient.

FIG. 10 illustrates how the preferred self-locking device 136 connects cords 40, 40' together. Although not illustrated, a second anchor 38' has been secured to the bronchial passageway at a place distant from that where the first anchor 38 is positioned. The second line 40' is attached to the second anchor 38'. As shown in FIGS. 10–13, the tube 34 may be used to force the self-locking device 136 towards the anchors 38, 38' to pull the anchors via the cords 40, 40'. The self locking device 136 may also be released from the inside of the tube 34, such as from the airway of a bronchoscope. Because the free ends 41, 41' of the cords 40, 40' are held taut, as the self-locking device 136 is moved toward the anchors 38, 38', the cords 40, 40' move relative to the self-locking device. As the self-locking device 136 is moved closer and closer to the anchors 38, 38', the cords 40, 40' can be pulled or further tensioned to reduce the anchor distance $L_{AD}$.

As shown in FIG. 10, and as described earlier in greater detail, the self-locking device or chock device 136 cinches-up on the cords 40, 40' and holds them in place while they are pulled and/or while the self-locking device is pushed toward the anchors. Because the self-locking device 136 automatically prevents the cords 40, 40' from reversing direction back toward the anchors 38, 38', once the desired reduced anchor distance $L_{AD}$ has been obtained, the self-locking device 136 automatically connects the cords 40, 40' to each other such that the reduced anchor distance $L_{AD}$ is maintained. Thus, there is no need to manually connect the cords 40, 40' to each other with a clasp or other connecting device 36. The more the anchors 38, 38' are pulled toward the self-locking device 136 (generally located at the median between the anchors) via the lines 40, 40', the more the lung tissue will collapse inward.

Although only two anchors are illustrated in FIGS. 11–13, more anchors can be used to further collapse or compress the volume of a portion of the lung. For example, three anchors may be spaced approximately 120 degrees apart from each other such that the anchors 38 each tension an equal portion of the area to be collapsed. In this manner, a larger portion of the lung may be collapsed, thus reducing the volume of the lung to a greater extent.

Figure 20:
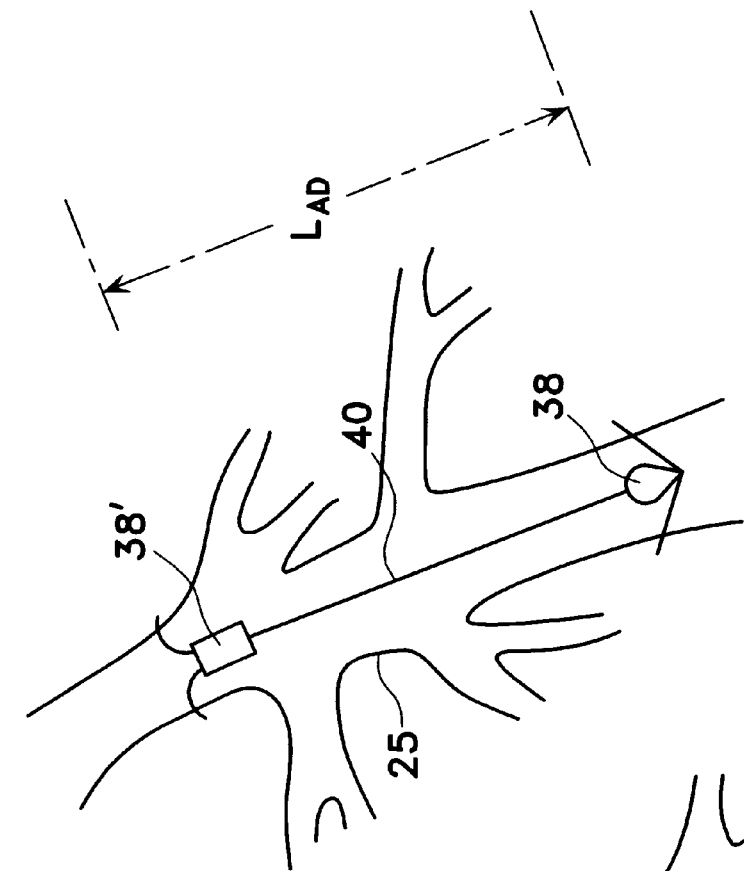
FIG. 20 is an illustration of the portion of the lung of FIG. 19 after its volume has been compressed.
Figure 19:
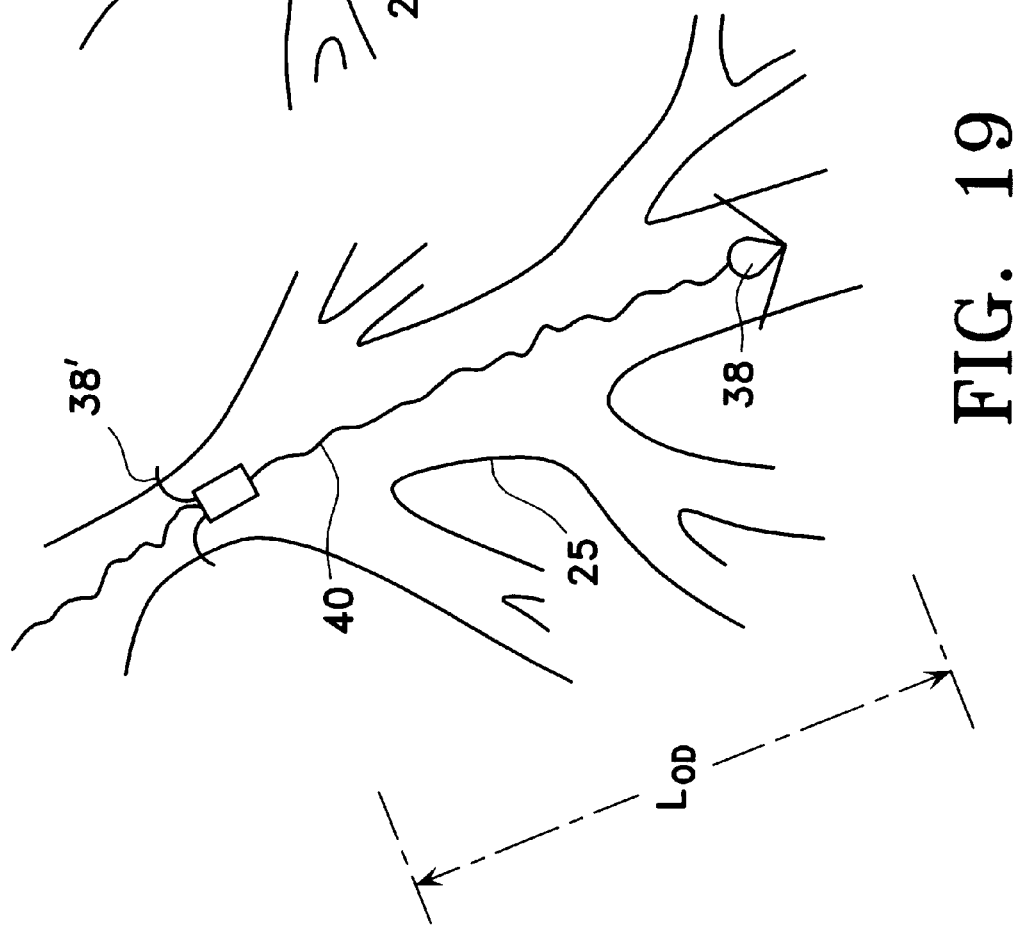
FIG. 19 is an illustration of a portion of a lung before its volume has been compressed.

Additionally, as illustrated in FIGS. 19 and 20, the distance between two anchors 38, 38' can be decreased by pulling or tensioning one cord 40, rather than two cords. For example, the first anchor 38 is be anchored or fixed at a first location and a second anchor 38' is fixed or located at a second location. The first anchor 38 and the second anchor 38' are separated by an original distance $L_{OD}$. The cord 40 is attached to the anchor 38 before it has been anchored. Alternatively, the cord 40 can be attached to the first anchor 38 after the anchor 38 has been anchored at the first position. In FIG. 19, the cord 40 is slack or limp, and the anchors 38, 38' are in their original positions.

As illustrated by FIG. 20, the cord 40 is pulled to decrease the distance between the anchors 38, 38' or move one anchor 38 toward the other anchor 38'. The cord 40 is placed in tension to pull the anchor 38 toward the anchor 38' to defined the anchor distance $L_{AD}$ which is less than the original distance $L_{OD}$. Thereafter, the tensioned cord 40 can be attached to the second anchor 38' such that the distance between the first anchor 38 and the second anchor 38' is not permitted to return to the original distance. The remaining non-functional portion of the cord 40 has been removed by cutting the cord 40 at a location directly adjacent to the anchor 38 and then pulling the excess cord from the lung. As shown in FIGS, 19 and 20, the second anchor 38' is a self-locking device, such as that shown in FIGS. 17 and 18, but has barbs such that it also is an anchor. Thus, the distance between the two anchored anchors 38, 38' can be reduced by pulling one cord 40 to compress the volume of a portion of the lung.

Furthermore, the cords can be an elastic device that regains its original shape after compression or extension, such as a coil of wire that keeps anchors attached thereto under constant tension. The cord can provide a constant or discontinuous tensile force to the anchors. For example, the cord can be an elastic filament such as a rubber band, or a collapsible spring.

The connection device 36, 136 and its components, the anchor 38, 138, and the line 40 may be made from a chemically inert and biocompatible, natural, or synthetic material which is well known in the art. Such material is preferably a non-bioerodable material which will remain in the patient after use, such as titanium or a titanium alloy. Generally, preferred materials are those acceptable for human implants. In general, typical materials of construction suitable for the above-mentioned items include non-reactive polymers or biocompatible metals or alloys. Metallic materials useful include stainless steel, platinum, tantalum, gold, and their alloys, as well as gold-plated ferrous alloys, platinum-plated ferrous alloys, cobalt-chromium alloys, and titanium nitride coated stainless steel. For example, the cables can be made from nylon, and the anchors can be made from a titanium alloy. The cables can be made from elastic materials such as an elastomer that is stretchable like a rubber band.

The network of alveoli in lungs provides strength to the airway walls, as well as elasticity to the lungs, both of which contribute to the lung's ability to function effectively. In cases of severe chronic pulmonary disease, such as emphysema, lung tissue is destroyed, reducing the strength of the airways. This reduction and strength of the airway walls allows the walls to become "floppy" thereby losing their ability to remain open during exhalation. In this diseased state, the patient suffers from the inability to get the air out of their lungs due to the collapse of the airways during exhalation. Heavily diseased areas of the lung become overinflated. Within the confines of the chest cavity, this overinflation restricts the in-flow of fresh air and the proper function of healthier tissue, resulting in significant breathlessness.

The present invention strives to address the above problems of overinflated and inefficient lung tissue in patients by compressing the volume of a severely diseased area of the lung, allowing the remaining healthier tissue to function more efficiently and improve patient breathing. Because the diseased portion of the lung has been collapsed or compressed, the remaining healthy tissue is redistributed, improving air exchange. According to one embodiment of the present invention, a plurality of anchors are lodged in the lung near the most distal part of the bronchial passageways of the lung. The anchors are drawn towards one another to cause the lung to collapse, thus compressing the airflow tissue in the lung and establishing a permanent reduction in lung volume. All of this is accomplished by a technique that is not nearly as invasive as prior art techniques for addressing this problem. The technique performed by the present invention can be performed without making a single incision. Accordingly, the risk of serious post-operative complications is lessened.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims be embraced thereby.

What is claimed is:

1. A method for compressing the volume of a portion of a lung, the method comprising:
   anchoring a first anchor at a first position in the lung;
   anchoring a second anchor at a second position in the lung, the first position being distant from the second position;
   reducing the distance between the anchored first anchor and the anchored second anchor; and
   preventing the reduced distance from substantially increasing.

2. The method according to claim 1, further comprising attaching a first cord to the first anchor and attaching a second cord to the second anchor.

3. The method according to claim 1, wherein a first cord is attached to the first anchor and a second cord is attached to the second anchor, and the distance is prevented from substantially increasing by connecting the first cord to the second cord after the distance has been reduced.

4. The method according to claim 1, wherein a first cord is attached to the first anchor and a second cord is attached to the second anchor, and the distance is reduced between the anchored first anchor and the anchored second anchor by causing relative motion between at least one of the cords and a self-locking device.

5. The method according to claim 1, wherein a first cord is attached to the first anchor and a second cord is attached to the second anchor, the step of reducing the distance between the anchored first anchor and the anchored second anchor includes pulling at least one of the first cord and the second cord to reduce the distance between the anchors.

6. The method according to claim 1, wherein the step of preventing the reduced distance from substantially increasing includes connecting the first anchor to the second anchor with a cord.

7. The method according to claim 1, further comprising:
anchoring a third anchor at a third position in the lung, the third position distant form the first position and the second position;
reducing the distance between the anchored first anchor and the anchored third anchor to decrease the volume of the lung; and
preventing the reduced distance between the first and third anchors from substantially increasing.

8. A method for compressing the volume of a portion of a lung, the method comprising:
anchoring in a portion of a lung an anchor having a cord attached thereto; and
pulling the cord to cause the anchor to pull on the portion of the lung to compress the volume of the portion of the lung.

9. The method according to claim 8, wherein the anchor is a first anchor and the cord is a first cord, further comprising anchoring a second anchor having a second cord attached thereto in a second portion of the lung;
pulling the second cord attached to the second anchor to cause the second anchor to pull on the second portion of the lung.

10. The method according to claim 9, further comprising cutting the first cord and a second cord to decrease a length of the first cord and the second cord.

11. The method according to claim 9, further comprising passing the first cord and the second cord through a self-locking device, wherein the pulling of the first cord and the pulling of the second cord are performed by pulling the first cord and the second cord through the self-locking device.

12. The method according to claim 8, wherein the anchor is anchored to a bronchial passageway.

13. The method according to claim 9, further comprising connecting the first cord to the second cord.

14. The method according to claim 9, wherein the pulling of at least one of the first cord and the second cord causes relative motion between the first anchor and the second anchor in a direction towards each other.

15. The method according to claim 9, wherein the first cord is pulled before the second cord is pulled.

16. The method according to claim 9, wherein the first cord and the second cord are pulled simultaneously.

17. The method according to claim 9, wherein the first cord has a first cord length measured between the anchor and a point of connection, the second cord has a second cord length measured between the anchor and the point of connection, wherein the tensioning of the first cord and the second cord are performed by decreasing the first cord length and the second cord length.

18. The method according to claim 8, further comprising located the anchor in the lung by inserting into a bronchial passageway of the lung a bronchoscope having the anchor therein, and then releasing the anchor from the bronchoscope at the portion of the lung to anchor the anchor in the lung.

19. The method according to claim 9, wherein the pulling of at least one of the first cord and the second cord causes an anchor length $L_{AD}$ to decrease.

20. An assembly for compressing the volume of a portion of a lung, the assembly comprising:
a first cord;
a first anchor in the form of a deformable spring for anchoring to a first portion of the lung, the first cord attached to the first anchor;
a second cord;
a second anchor in the form of a deformable spring for anchoring to a second portion of the lung, the second cord being attached to the second anchor;
a delivery device for delivering the first anchor to the first portion of the lung and for delivering the second anchor to the second portion of the lung; and
a connection device for connecting the first cord to the second cord within the lung.

21. The assembly according to claim 20, wherein the delivery device is a tube.

22. The assembly according to claim 20, wherein the first anchor and the second anchor are V-shaped springs.

23. The assembly according to claim 20, wherein the connection device includes a self-locking device.

24. The assembly according to claim 20, wherein the first cord has a first cord length measured between the first anchor and the connection device, the second cord has a second cord length measured between the second anchor and the connection device, the connection device preventing the first cord length and the second cord length from increasing.

25. An assembly for compressing the volume of a portion of a lung, the assembly comprising:
a first anchor for anchoring to a first portion of the bronchial passageways of the lung, the first anchor being deformable from an insertion configuration to an expanded anchoring configuration;
a second anchor for anchoring to a second portion of the bronchial passageways of the lung, the second anchor being deformable from an insertion configuration to an expanded anchoring configuration;
a connection device for positioning in the lung;
a first cord connecting the first anchor to the connection device; and
a second cord connecting the second anchor to the connection device, the connection device preventing the first cord and the second cord from moving relative to the connection device in a direction away from the connection device.

26. The assembly according to claim 25, wherein the connection device is a self-locking device, at least one of the first cord and the second cord wedgeable in the self-locking device such that the one cord is prevented from moving relative to the self-locking device in the direction away from the connection device and is permitted to move in an opposite direction.

27. The assembly according to claim 25, wherein the direction away from the self-locking device is toward one of the first and second anchors.

28. The assembly according to claim 25, wherein the first and second anchors include V-shaped springs.

29. An assembly for compressing the volume of a portion of a lung, the assembly comprising:
a first anchor for anchoring to a first portion of the lung;
a second anchor for anchoring to a second portion of the lung;
a third anchor for anchoring to a third portion of the lung;
a connection device connected to the first anchor by a first cord, connected to the second anchor by a second cord, and connected to the third anchor by a third cord, the first cord having a first cord length measured between the first anchor and the connection device, the second cord having a second cord length measured between the second anchor and the connection device, the third cord having a third cord length measured between the third anchor and the connection device, the connection device preventing the first cord length, the second cord length, and the third cord length from increasing.

30. The assembly according to claim 29, wherein the connection device permits the first cord length and the second cord length to decrease.

31. The assembly according to claim 29, wherein the first anchor and the second anchor include barbs.

32. The assembly according to claim 29, wherein the connection device is located between the first anchor and the second anchor.

33. A method for compressing the volume of a portion of a lung, the method comprising:

connecting the first anchor to the second anchor with at least one cord;

fixing the first anchor at a first portion of the lung;

fixing the second anchor at a second portion of the lung; and tensioning the at least one cord to cause at least one of the first anchor and the second anchor to decrease the volume of the lung.

34. The method according to claim 33, wherein the anchors are connected with two cords after the first anchor has been fixed at said first position and the second anchor has been fixed at said second position.

35. The method according to claim 33, wherein the at least one cord is tensioned after the first anchor is fixed at said first position and before the second anchor is fixed at said second position.

36. An assembly for compressing the volume of a portion of a lung, the assembly comprising:

a first deformable anchor for anchoring to a first portion of the lung;

a second deformable anchor for anchoring to a second portion of the lung; and a cord for attaching the first anchor to the second anchor.

37. The assembly according to claim 36, wherein the cord includes two cords that are connected to each other.

38. The assembly according to claim 37, wherein the two cords are connected to each other with a connecting device.

39. The assembly according to claim 36, wherein the cord is elastic.

40. The assembly according to claim 36, wherein the cord is attached to the first anchor.

41. The assembly according to claim 36, wherein the first anchor is a V-shaped spring.

42. The assembly according to claim 36, wherein the first anchor is a self-locking device.

43. The assembly according to claim 36, further comprising a device for anchoring the first and second anchors in the lung.

44. The assembly according to claim 20, further comprising a third cord and a third anchor for anchoring to a third portion of the lung, the third cord attached to the third anchor and connected to the connection device.

45. The assembly according to claim 25, further comprising a third anchor for anchoring to a third portion of the bronchial passageways of the lung.

46. The assembly according to claim 36, further comprising a third anchor for anchoring to a third portion of the lung, the cord attaching the first anchor, the second anchor, and the third anchor.

47. The assembly according to claim 36, wherein the first deformable anchor and the second deformable anchor each include two flexible barbs.

* * * * *